United States Patent [19]

Bisconte de Saint Julien

[11] Patent Number: 5,828,716

[45] Date of Patent: Oct. 27, 1998

[54] PROCEDURE FOR IDENTIFYING THE NUMBER OF PARTICLES THAT ARE WEAKLY LUMINESCENT

[75] Inventor: Jean-Claude Bisconte de Saint Julien, Brijs Sous Forges, France

[73] Assignee: Biocom S.A., Les Ulis Cedex, France

[21] Appl. No.: 662,312

[22] Filed: Jun. 12, 1996

[51] Int. Cl.$^6$ .................................................. G06M 11/02
[52] U.S. Cl. .............................................. 377/10; 377/11
[58] Field of Search ........................................ 377/10, 11

[56] References Cited

U.S. PATENT DOCUMENTS 5,274,431  12/1993  Kuroda ........................................ 377/10
5,365,559  11/1994  Hsueh et al. ............................... 377/10
5,426,501  6/1995  Hokanson et al. ........................ 377/11

*Primary Examiner*—Margaret Rose Wambach
*Attorney, Agent, or Firm*—Weiser & Associates, P.C.

[57] ABSTRACT

The present invention relates to a procedure for counting faintly luminescent particles, and relates specifically to a procedure for counting cells and microorganisms marked with a colored or fluorescent stain or marker that selectively marks the microorganisms and cells to be counted, characterized by the fact that the said procedure is implemented with the aid of a photon-accumulator camera and includes the acquisition of at least one low-resolution image I, the threshold processing of the said low-resolution image in order to obtain at least one digital image Ib, at least one dimensional filtration stage, and the counting of the number N of objects belonging to a given class of sizes in the digital image Ib.

16 Claims, 3 Drawing Sheets

DURATION OF THE ACQUISITION TIME

PROCEDURE FOR IDENTIFYING THE NUMBER OF PARTICLES THAT ARE WEAKLY LUMINESCENT

BACKGROUND OF THE INVENTION

1. Field of the Invention

The present invention relates to a procedure for counting faintly luminescent particles, and relates specifically to a procedure for counting cells and microorganisms marked with a colored or fluorescent stain or marker that selectively marks the microorganisms and cells to be counted.

2. Description of the Related Art

The procedures in accordance with the state of the art consist of acquiring an image at a high level of magnification and proceeding with an analysis of this image after shape-recognition data-processing treatment, such as for example contour-recognition treatment. Because of the high level of magnification necessary to obtain detailed images of the objects to be counted, and because of the very low density of the objects, it is necessary to explore a large number of fields in a sample and then to proceed with a statistical analysis in order to deduce the density of the objects in the sample.

The development of automatic equipment indicates that the natural tendency of those skilled in the art is continually to improve the individual counting of events, by evolving from the visual counting of the colonies formed by a culture on a nutrient medium in a Petri dish to the combination of filtration on a membrane and automatic counting by means of image processing, and then to the automation of the repositioning of the microscope along the X-Y axes and in terms of the depth of field, in order to multiply the number of fields analyzed. Another approach, which is also based on the principle of the individual counting of events and that is known under the name "flow cytometry" consists of counting individually the passage of an event in a carrier flow.

The individual counting of events is possible only through the use of improved optical means that guarantee a high level of discrimination among objects. A video camera is customarily used, in conjunction with a microscope that has a high level of magnification which allows a very detailed image to be obtained, which therefore covers a minutely small portion of the sample. These high-performance (and therefore fragile) optics are associated with high-performance mechanical means that enable three-dimensional micro-repositioning of the sample-carrier plate in relation to the objective lens, in such a way as to allow a statistically significant number of fields to be scanned. Therefore, there is no question but that the improvement in reliability is manifested by an increase in the sophistication of optical and mechanical performance, and is also manifested by a high cost and the need for delicate handling outside the laboratory.

SUMMARY OF THE INVENTION

The present invention is radically opposed to this trend that consists of improving techniques for the individual counting of events, by proposing quite to the contrary the acquisition of an image of marked microorganisms and cells located on a substrate under low magnification, doing so by means of a device that generates images by accumulating and counting photons, referred to in the specification as a photon-accumulator camera. As used in this context, the term "low magnification" refers to a level of magnification that is distinctly lower than that of the type of microscope that is customarily utilized in conjunction with state-of-the-art unit-based counting devices, such as for example a magnification power of less than 100.

In accordance with the invention, with the aid of a photon-accumulator camera, during a time interval that is short in relation to the speed of development of the luminescent particles, a plurality of images $I_i$ are acquired, which images correspond to different acquisition times. Threshold processing is then performed for each of the images $I_i$ in order to obtain digital images $I_{bi}$. At least one dimensional filtration stage is performed, and the number $N_i$ of objects belonging to a given class of sizes in each of the digital images $I_{bi}$ is counted, with the number of luminescent particles corresponding to the maximum value of $N_i$.

The accumulator camera delivers a signal whose dynamics are very high and which, in conjunction with digital processing, allows an accurate result to be obtained in spite of the low resolution. In particular, acquisition of an image by a photon-accumulator camera allows the focusing step to be omitted, and also allows work to be performed on the field of observation in a simultaneous and homogeneous manner.

The accumulation of photons and the implementation of the procedure in accordance with the invention make it possible to obtain processable information from images whose resolution is extremely mediocre and that therefore cover an extended area of the field.

A low level of magnification, such as for example 4, allows the photons to be counted but under no circumstances allows the bacteria to be recognized. Recourse to low-resolution image-acquisition means, under a low level of magnification—which flies in the face of the teaching of the procedures and apparatus in accordance with the state of the art—offers certain essential advantages.

In the first place, the problems associated with focusing are considerably simplified, or even eliminated. The procedures in accordance with the state of the art implement extremely complex means in order to ensure perfect focusing on the plane associated with the objects to be counted, and often require the successive scanning of several successive focal planes for a given field of observation. Consequently, the counting time is significantly longer.

In the second place, the acquisition of low-resolution images makes it possible to explore an extended field area of the sample, or even the entire area of a sample. Because the objects to be counted are usually located very far apart, this advantage is decisive. In fact, the procedures in accordance with the state of the art are usually content to explore a statistically representative number of fields, rather than the entire area of the sample. For phenomena that display a significant standard deviation because of the presence of artifacts (such as agglomerations of particles or a non-homogeneous distribution of objects in the sample), this approach is unquestionably less satisfactory than the procedure in accordance with the invention, which allows a complete acquisition of the entirety of the sample.

In the third place, the digital processing step involves primarily digital images, and essentially relates to a class of digital images of objects as a function of their size. The digital processing step implements simple algorithms, and does not require any significant amounts of computing power or time, unlike the procedures in accordance with the state of the art, which are based on cumbersome shape-recognition methods and complex processing operations that consume a large amount of computation time.

In the fourth place, it is possible to utilize a source for the excitation of the low-fluorescence, thereby avoiding "burning" the markers. This advantage is important, because by avoiding the degradation of the markers during the counting operation, the samples can be preserved and measurement verification operations can be performed at a later time.

In accordance with a first variant, the dimensional filtration involves the objects in the digital image occupying a surface area that is greater than the apparent nominal cross-section of the particles to be counted.

In accordance with a second variant, the dimensional filtration involves the objects in the digital image occupying a surface area that is essentially equal to the apparent nominal cross-section of the particles to be counted.

In accordance with one particular embodiment, several classes of objects are determined so that particles of different types can be counted.

The invention also relates to an installation or apparatus for counting faintly luminescent particles, in particular, to a procedure for counting cells and microorganisms marked with a colored or fluorescent stain or marker that selectively marks the microorganisms and cells to be counted, which installation or apparatus includes a source for the excitation of the luminescent particles and a photon-accumulator camera associated with optics with low magnification that are suitable for forming an image of the analyzed sample, with the resolution of the image being sufficient to allow the apparent image of the particles to be counted to occupy several pixels. The accumulator camera is controlled by a microcomputer, in such a way that a plurality of images Ii are obtained that correspond to different acquisition times, with the signal provided by the camera being analyzed in such a way as to allow particles of one or more given types to be counted.

The signal delivered by the accumulator camera, which signal corresponds to each of the image, is processed by a microcomputer that performs a thresholding operation in order to obtain digital images Ibi; and the said procedure includes at least one dimensional filtration stage and the counting of the number Ni of objects belonging to a given class of sizes in each of the digital images Ibi, with the number of luminescent particles corresponding to the maximum value of Ni.

In accordance with a preferred embodiment, the accumulator camera is associated with optics whose magnification power is less than 40.

In accordance with one particular embodiment, the samples are carried by a belt or band that advances in a sequential manner under the optics associated with the photon-accumulator camera.

In accordance with one particular variant of an embodiment, the installation or apparatus in accordance with the invention includes a device for the preparation of the samples, which device comprises a belt or band that advances in a sequential manner, with the belt or band being formed through the association of a filtration layer and a protective film, with the belt or band passing successively under means that are appropriate for depositing a fluid containing the particles to be counted, under means that are appropriate for delivering a nominal quantity of a marking reagent, under suction means, and then under the counting means.

BRIEF DESCRIPTION OF THE DRAWINGS

The following description of the invention will be better understood through reference to the attached drawings, on which.

DETAILED DESCRIPTION

Figure 1:
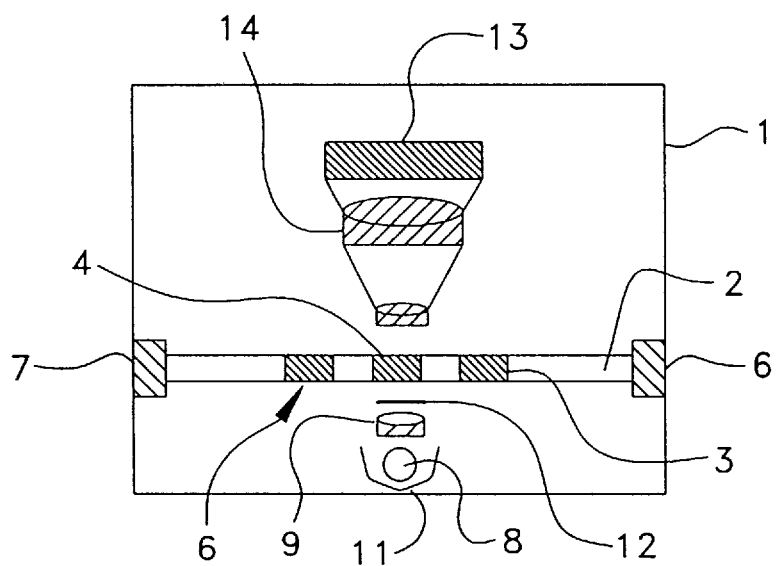
FIG. 1 represents a cross-sectional view of a first example of an embodiment of an installation or apparatus in accordance with the invention.

FIG. 1 represents a schematic cross-sectional view of an example of an embodiment of an installation or apparatus for counting cells in accordance with the invention. The counting is done starting with a microporous membrane 2 that contains a matrix of filtration zones 3, 4, 5, whose configuration is determined by the filtration device employed, which for example may be a filtration module of the type available commercially from the BIOMERIEUX company under the name COBRA (a registered trademark).

The sample is prepared in accordance with a known procedure, by means of filtration and staining.

The apparatus includes a rigid and opaque housing 1 that contains a trapdoor opening which allows the introduction of a microporous membrane 2 into a flexible indexed substrate that carries filtrates 3, 4, 5. The membrane 2 is placed on a metal carrier that forms a sliding drawer mounted between two guide rails 6, 7.

A source of ultraviolet radiation 8 associated with a condenser 9 is placed below the drawer carrying the membrane 2. A bandpass filter 11 that allows the UV rays to pass that are on the excitation wavelength of the markers is intercalated between the ramp for the UV sources 8 and the membrane 2. A metallized reflector 12 sends a portion of the radiation toward the filter 11.

On the side opposite the UV ramp, the apparatus includes a photon-accumulator sensor 13 associated with a lens block 14 that has a magnification power on the order of 10, and preferably between 4 and 40.

The photon-accumulator sensor includes, for example, 768×562 pixels, each consisting of 256 bits.

Figure 2:
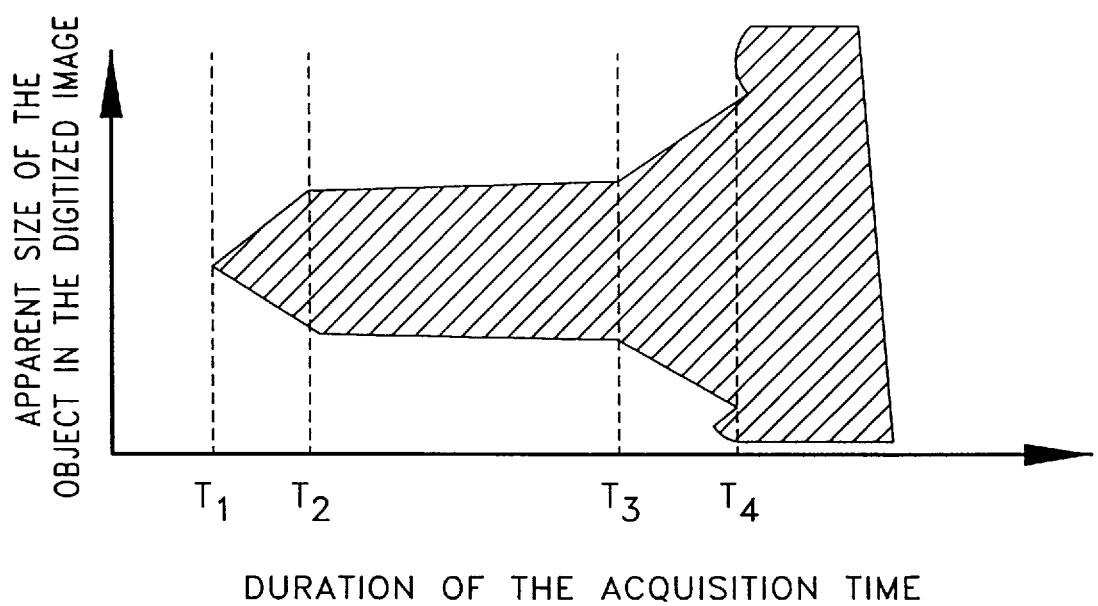
FIG. 2 represents the curve for the evolution of the apparent size of the object as a function of the acquisition time.

FIG. 2 represents the curve for the evolution of the apparent size of the object in the digitized image, as a function of the acquisition time.

For an acquisition period of less than a given time T1, the photon-accumulation camera does not detect any photons, or else detects a number of photons that is below the threshold value that was determined in order to digitize the image.

For an acquisition period between T1 and T2, the size of the object increases, essentially proportionally to the duration of the acquisition time T. This range of times contains a cone indicating the appearance of the object, whose position on the digitized image of the point corresponds essentially to the center of gravity of the luminescent object.

For an acquisition time between T2 and T3, the size of the object remains essentially constant or else increases slightly. The apparent size of the light "spot" corresponds essentially to the apparent size of the luminescent object. This zone will be referred to hereinafter as the "nominal cone".

This range of acquisition times is relatively extended, and corresponds to the range of times for which the counting of the digitized objects that fall within a predefined class of sizes will represent the number of luminescent objects in the sample.

For an acquisition time between T3 and T4, the size of the apparent object increases rapidly, because of the phenomena associated with the diffusion of the light emitted by the object of the sample. This range includes a diffusion cone with a steep slope.

Beyond an acquisition time T4, the size of the spot increases very rapidly, until a saturation threshold for the sensor is reached. This zone corresponds to the background luminosity, which can be detected for very long duration acquisition times, and to the noise phenomena inherent in the acquisition camera.

The optimal duration of the acquisition time will vary from one object to another, depending on the intensity of the luminosity. However, the range of acquisition times between T2 and T3 is sufficiently large to include, for at least one of the images Ii, the beginning of the nominal cone for the objects with very faint luminosity and also the end of the nominal cone for highly luminescent objects.

Figure 3:
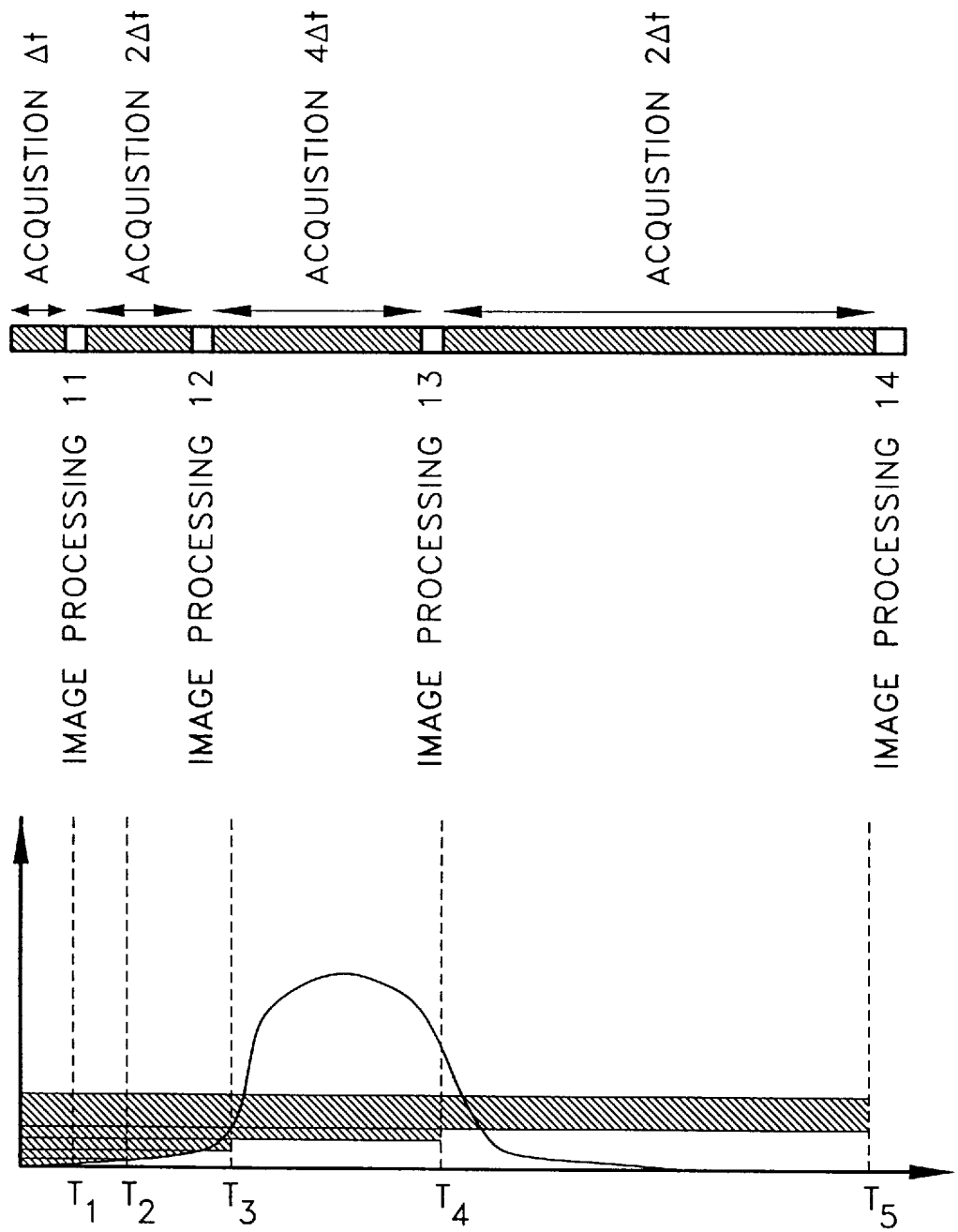
FIG. 3 shows a sequential diagram of the counting procedure.

For this purpose, as indicated schematically in FIG. 3, an acquisition "burst" is implemented for various periods of time, for example, crossing times. The sequence of the acquisition periods is not critical. This sequence may consist of a geometric progression, in order to optimize the amount of time necessary to obtain a satisfactory image. The overall duration of the acquisition burst will be brief in relation to the development of the observed phenomena, and particularly in relation to the weakening of the luminescence or in relation to the variation in the excitation light.

The filtration consists of digital processing of the digitized image. All of the objects in the digitized image are counted whose size (i.e., the number of adjacent pixels) complies with a given function.

For example, this function may be the function entitled "greater than N pixels", where "N pixels" corresponds to the mean value of the apparent cross-section of an object to be counted, or else may be "between N−ε and N+ε pixels".

The result is indicated by a function represented schematically in FIG. 3, which function corresponds to a Gaussian curve.

The processing of the image delivered after each acquisition may be done in real time, or else in non-clock-dependent time. In the latter case, each image Ii is stored in memory, and each of the stored images is processed at the end of the acquisition burst.

Figure 4:
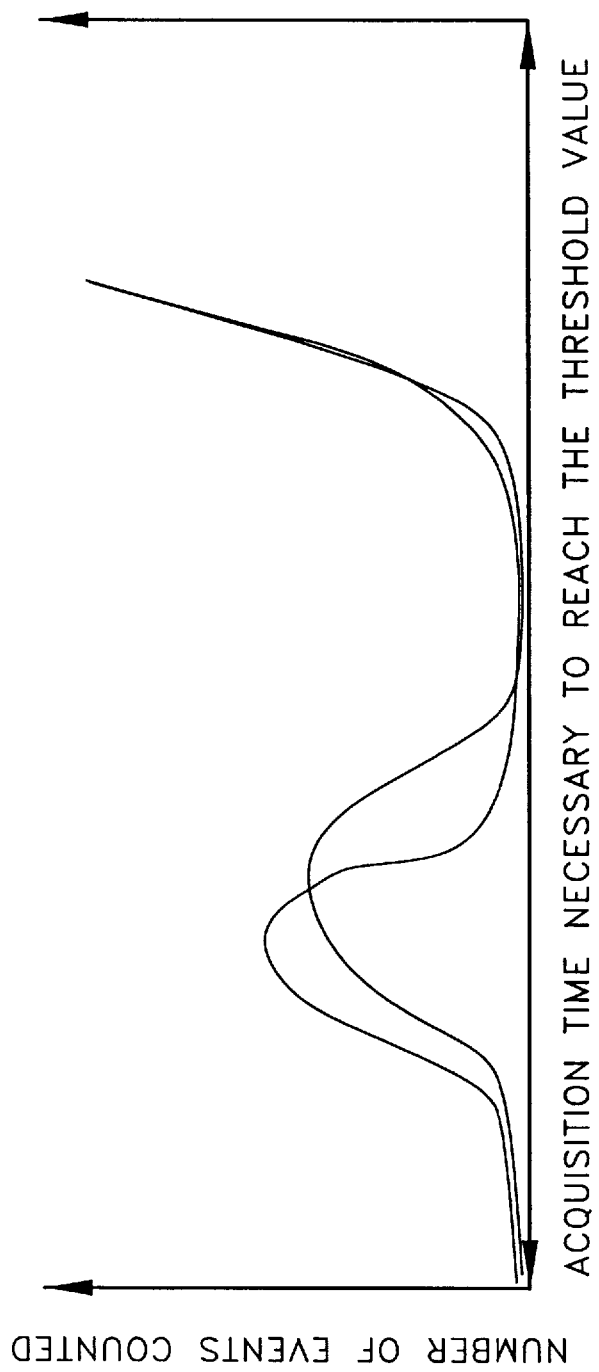
FIG. 4 represents the curve for the "luminosity fluorescence" function.

FIG. 4 represents the curve for the length of the acquisition period that is necessary in order for the threshold value Vs to be reached, which value was implemented for the digitization of the acquired image as a function of the luminosity of the objects.

The curve contains a first bell-shaped zone and a divergent portion that corresponds to the background luminosity. The bell-shaped portion is shifted toward the divergent portion when the fluorescence of the objects is lower.

In accordance with one particular variant, the invention relates to an installation or apparatus that allows continuous examinations to be performed.

The samples are placed on a moving strip of film formed by a layer of substrate material, for example, a plastic material such as polyethylene, on which is deposited a second layer of a film forming a filter. An upper protective film contains perforations at regular intervals in order to provide disk-shaped filtration zones.

The film is wound around a spool. It is unrolled sequentially in such a way that a given filtration zone passes successively under means for depositing samples, under one or more means for depositing reagents, then through a suction zone that is suitable for ensuring the concentration, on the filter, of the objects to be counted, and finally through an observation zone. The film substrate is separated from the filtration film before the film passes into the suction zone.

The foregoing description of the invention has been offered as a non-limitative example. Those skilled in the art will be able to implement various variants without, in so doing, departing from the scope of the invention.

I claim:

1. A procedure for counting faintly luminescent particles marked with a colored or fluorescent stain or marker that selectively marks the particles to be counted with the aid of a photon-accumulator camera, comprising the steps of:
   (a) acquiring at least one low-resolution image I;
   (b) threshold processing of the low-resolution image in order to obtain at least one digital image Ib;
   (c) performing at least one dimensional filtration stage on the digital image; and
   (d) counting the number N of objects belonging to a given class of sizes in the digital image Ib.

2. The procedure of claim 1, wherein the procedure is implemented during a time interval that is short in relation to the speed of development of the luminescent particles; and includes acquiring a plurality of images Ii corresponding to different acquisition times, threshold processing for each of the images Ii in order to obtain digital images Ibi, performing at least one dimensional filtration stage on each digital image, and the counting of the number Ni of objects belonging to a given class of sizes in each of the digital images Ibi, with the number of luminescent particles corresponding to the maximum value of Ni.

3. The procedure of claim 2, wherein the dimensional filtration stage involves the objects in the digital image occupying a surface area greater than the apparent nominal cross-section of the particles to be counted.

4. The procedure of claim 2, wherein the dimensional filtration stage involves the objects in the digital image occupying a surface area that is essentially equal to the apparent nominal cross-section of the particles to be counted.

5. The procedure of claim 4, wherein several classes of objects are determined so that particles of different types can be counted.

6. The procedure of claim 3, wherein several classes of objects are determined so that particles of different types can be counted.

7. The procedure of claim 2, wherein several classes of objects are determined so that particles of different types can be counted.

8. The procedure of claim 1, wherein several classes of objects are determined so that particles of different types can be counted.

9. An apparatus for counting faintly luminescent particles marked with a colored or fluorescent stain or marker that selectively marks the particles to be counted, comprising:
   (a) a source for the excitation of the luminescent particles;
   (b) a photon-accumulator camera associated with optics with low magnification that are suitable for forming an image of the analyzed sample, with the resolution of the image being sufficient to allow the apparent image of the particles to be counted to occupy several pixels; and
   (c) a microcomputer adapted to control the accumulator camera in such a way that a plurality of images Ii are obtained that correspond to different acquisition times, with the signal provided by the camera being analyzed in such a way as to allow particles of one or more given types to be counted.

10. The apparatus of claim 9, wherein the samples are carried by a belt or band that advances in a sequential manner under the optics associated with the photon-accumulator camera.

11. The apparatus of claim 10, wherein the apparatus includes a device for preparing the samples, which device comprises a belt or band that advances in a sequential manner, with the belt or band being formed through the association of a filtration layer and a protective film, with the belt or band passing successively under means that are appropriate for depositing a fluid containing the particles to be counted, under means that are appropriate for delivering a nominal quantity of a marking reagent, under suction means, and then under the counting means.

12. The apparatus of claim 9, wherein the microcomputer is adapted to:

perform a thresholding operation on the signal delivered by the accumulator camera, which signal corresponds to each of the images Ii, in order to obtain digital images Ibi;

perform at least one dimensional filtration stage on the digital images Ibi; and count the number Ni of objects belonging to a given class of sizes in each of the digital images Ibi, with the number of luminescent particles corresponding to the maximum value of Ni.

13. The apparatus of claim 12, wherein the accumulator camera is associated with optics whose magnification power is less than 40.

14. The apparatus of claim 12, wherein the samples are carried by a belt or band that advances in a sequential manner under the optics associated with the photon-accumulator camera.

15. The apparatus of claim 9, wherein the accumulator camera is associated with optics whose magnification power is less than 40.

16. The apparatus of claim 15, wherein the samples are carried by a belt or band that advances in a sequential manner under the optics associated with the photon-accumulator camera.

* * * * *

UNITED STATES PATENT AND TRADEMARK OFFICE
CERTIFICATE OF CORRECTION

PATENT NO. : 5,828,716

DATED : October 27, 1998

INVENTOR(S) : Jean-Claude Bisconte de Saint Julien

It is certified that error appears in the above-identified patent and that said Letters Patent is hereby corrected as shown below:   On the title page: Item

[75] Inventor: Jean- Claude Bisconte de Saint Julien.
     Briis Sous Forges, France Signed and Sealed this Second Day of March, 1999

Attest:

Q. TODD DICKINSON

*Attesting Officer*    *Acting Commissioner of Patents and Trademarks*